United States Patent [19]
Fan

[11] Patent Number: 4,629,702
[45] Date of Patent: Dec. 16, 1986

[54] METHOD FOR CLASSIFYING THE SEDIMENTARY KEROGEN FOR OIL SOURCE

[75] Inventor: Mark J. Fan, Irving, Tex.

[73] Assignee: Mobil Oil Corporation, New York, N.Y.

[21] Appl. No.: 657,643

[22] Filed: Oct. 4, 1984

[51] Int. Cl.$^4$ ............................................. G01N 30/00
[52] U.S. Cl. ...................................... 436/32; 436/139; 436/155; 436/161
[58] Field of Search .................... 436/32, 29, 145, 140, 436/161, 158, 155, 139; 422/78, 80; 73/863.11

[56] References Cited

U.S. PATENT DOCUMENTS

| | | | |
|---|---|---|---|
| 2,437,045 | 3/1948 | Roper | 436/32 |
| 3,033,287 | 5/1962 | Bond | 436/32 |
| 3,305,317 | 2/1967 | Cooper et al. | 436/29 |
| 3,345,137 | 10/1967 | McAuliffe | 436/29 |
| 3,446,597 | 5/1969 | Bray et al. | 436/32 |
| 3,480,396 | 11/1969 | Knenvolden | 436/31 |
| 3,654,145 | 4/1972 | Brunnock et al. | 436/140 |
| 3,953,171 | 4/1976 | Espitalie et al. | 436/32 |
| 4,106,908 | 8/1978 | Leplat-Gryspeerdt | 422/80 |
| 4,344,917 | 8/1982 | Schorno | 422/78 |
| 4,357,836 | 11/1982 | Kokesh | 73/863.11 |

FOREIGN PATENT DOCUMENTS

2716120  10/1977  Fed. Rep. of Germany ........ 436/32
8303676  10/1983  United Kingdom ................ 436/155

Primary Examiner—S. Leon Bashore
Assistant Examiner—V. Manoharan
Attorney, Agent, or Firm—A. J. McKillop; Michael G. Gilman; Charles A. Malone

[57] ABSTRACT

A method for classifying kerogenous materials, e.g. materials found in raw rocks, sediments, and the like, is disclosed which comprises pyrolyzing a sample containing said materials, and analyzing the pyrolysis gases by gas chromatography and classifying the kerogen by type, i.e., oily, coaly, or mixed type, based upon selected hydrocarbon ratios.

8 Claims, 7 Drawing Figures

KEROGEN IDENTIFICATION OF 3 SERIES OF SAMPLES WHICH ARE ADJACENT TO A NEARBY IGNEOUS BODY

FIG. 7

SCHEMATIC DIAGRAM OF ANALYSES

PYROCHROMATOGRAPHIC ANALYSIS

METHOD FOR CLASSIFYING THE SEDIMENTARY KEROGEN FOR OIL SOURCE

FIELD OF THE INVENTION

This invention relates to a method for the chemical classification of kerogenous matter contained in sedimentary rocks. In one aspect, it relates to the determination of the quality of volatile hydrocarbons and the hydrocarbon-generating potential of the insoluble organic material or kerogen present in a geological sample. In another aspect, it relates to a method of analyzing geological samples to evaluate the petroleum-generating potential of the sample.

BACKGROUND OF THE INVENTION

Kerogen has long been an enigma and its meaningful classification an illusive goal.

In the field of geochemical research and petroleum exploration, an area of growing interest is analysis of geological samples to determine the remaining petroleum-generating potential of the rock sample. Work in this field has been directed to methods for removing hydrocarbons from geological samples and analyzing the hydrocarbons, to apparatuses for laboratory and field analysis for geological samples, and to the development of theoretical and practical models for predicting petroleum-exploration-related characteristics for the raw data obtained.

A method known in the art for such analysis involves the thermal extraction of volatile hydrocarbons from a kerogen (insoluble organic portion of sedimentary rock) or rock samples under carefully controlled temperature conditions and the analysis of the hydrocarbons extracted. In this method, a geological sample is heated to about 280° C. at a constant rate of temperature increase. A gas-detecting instrument records signals representative of the quantity of both volatile hydrocarbons and other gases thermally extracted from the sample. The sample is further heated to a higher temperature at a constant rate of temperature increase. A gas-detecting instrument records signals representative of the quantity of hydrocarbons and inorganic gases formed by pyrolyses over some predetermined temperature range. The quantities of hydrocarbons formed can be expressed in units of milligrams hydrocarbon per grams sample. One such thermal method involves the controlled heating of a geological sample and the determination of the amount of hydrocarbons and non-hydrocarbons generated over at least two predetermined temperature ranges.

Other commonly utilized techniques for classifying kerogen lack certain of the virtues of the pyrolytic system. Visual characterization, although currently popular, of necessity, focuses on the larger size, more visible fraction of kerogen rather than the entire mixture, as is the case with pyrolysis. Attempts to relate visual characterization with pyrolytic determinations and chemical analysis have met with very limited success.

A more definitive method popularized by Tissot and now in common usage utilizes ratios of carbon, hydrogen, and oxygen to classify kerogens into three groups. However, when kerogens of diverse composition reach the mature stage, their composition, in terms of the ratios of carbon, hydrogen, and oxygen become more similar. This may cause the elemental ratio data for mature kerogens to lack capacity to support inferences of whether oil and/or gas were generated at earlier stages of maturity.

Therefore, what is needed is a method of classification which will have an advantage in terms of cost and simplicity of sample preparation. Also, what is needed is a method which would give more detail and significant data regarding the basic structure of a kerogen.

SUMMARY OF THE INVENTION

This invention discloses a method for classifying kerogenous materials by pyrolyzing a sample containing said material and analyzing the pyrolysis gases by gas chromatography. To accomplish this, a weighed sample of the crushed raw mineral material containing said kerogenous material is placed under an inert gas atmosphere at a temperature of from about 250° C. to about 350° C. After eluting the hydrocarbonaceous gas resulting from the pyrolyzed kerogenous material, a chromatogram is developed which shows the relationship of the various hydrocarbonaceous components emitted from said kerogenous material. Subsequently, the ratio of $C_1$ to $C_5$ hydrocarbons contained in said pyrolysis hydrocarbonaceous gas in relationship to $C_7$ to $C_{11}$ hydrocarbons is determined. Said ratios are then differentiated into groups containing a ratio of less than about 25, a ratio of about 25 to about 45, and a ratio of greater than about 45. Upon comparing the ratios of the various groups, said kerogenous material is classified according to said ratios into three principal groups.

Subclassifications are then developed within each of the three principal groups based on the ratio of $C_{1+2}/C_{3+4}$ pyrolytic paraffinic hydrocarbons. Kerogens consisting predominantly of molecular skeletons of lipid-derived materials produce gaseous hydrocarbons with $C_{1+2}/C_{3+4}$ ratios less than about 1.50, similar to humic substances. Oily kerogens with $C_{1+2}/C_{3+4}$ ratios greater than about 1.50 are considered to be dominated by humic structures. Coaly kerogens with $C_{1+2}/C_{3+4}$ ratios greater than about 5.0 yield abundant methane and ethane and appear to consist predominantly of lignin structures. Kerogens composed predominantly of organic material with cellulosic structures are within the group of coaly kerogens indicated by $C_{1+2}/C_{3+4}$ ratios less than about 5.0. Within the intermediate group of kerogens, $C_{1+2}/C_{3+4}$ ratios above about 1.5 indicate a predominance of cellulosic substances while ratios below about 1.5 suggests the presence of predominantly humic substances.

It is therefore an object of this invention to provide for a classification system which allows for utilization of an entire mixture of a small sample of kerogenous material.

It is a yet further object of this invention to provide a classification system based upon the chemical analysis of kerogen rather than a visual inspection thereof.

Another object of this invention is to provide for a method which allows for classification of kerogenous materials in a short period of time.

A still further object of this invention is to provide for a method which allows for simplicity of sample preparation.

A yet further object of this invention is to provide for a method of classifying kerogenous material which method is able to reveal the basic structure of kerogen.

DESCRIPTION OF THE PREFERRED EMBODIMENTS

Classification of source rock by pyrochromatography is promising because contaminants can be pre-extracted and small samples can be used satisfactorily for the analytical technique. This enables the analysis of samples from deep and hot wells using Invermul drilling fluid which contains about 70% oil. Also, side wall cores and cutting chips from sample libraries may be used, even if the samples are as small as one gram or less. The total analytical time for each sample, about 60 minutes, is short.

Figure 7:
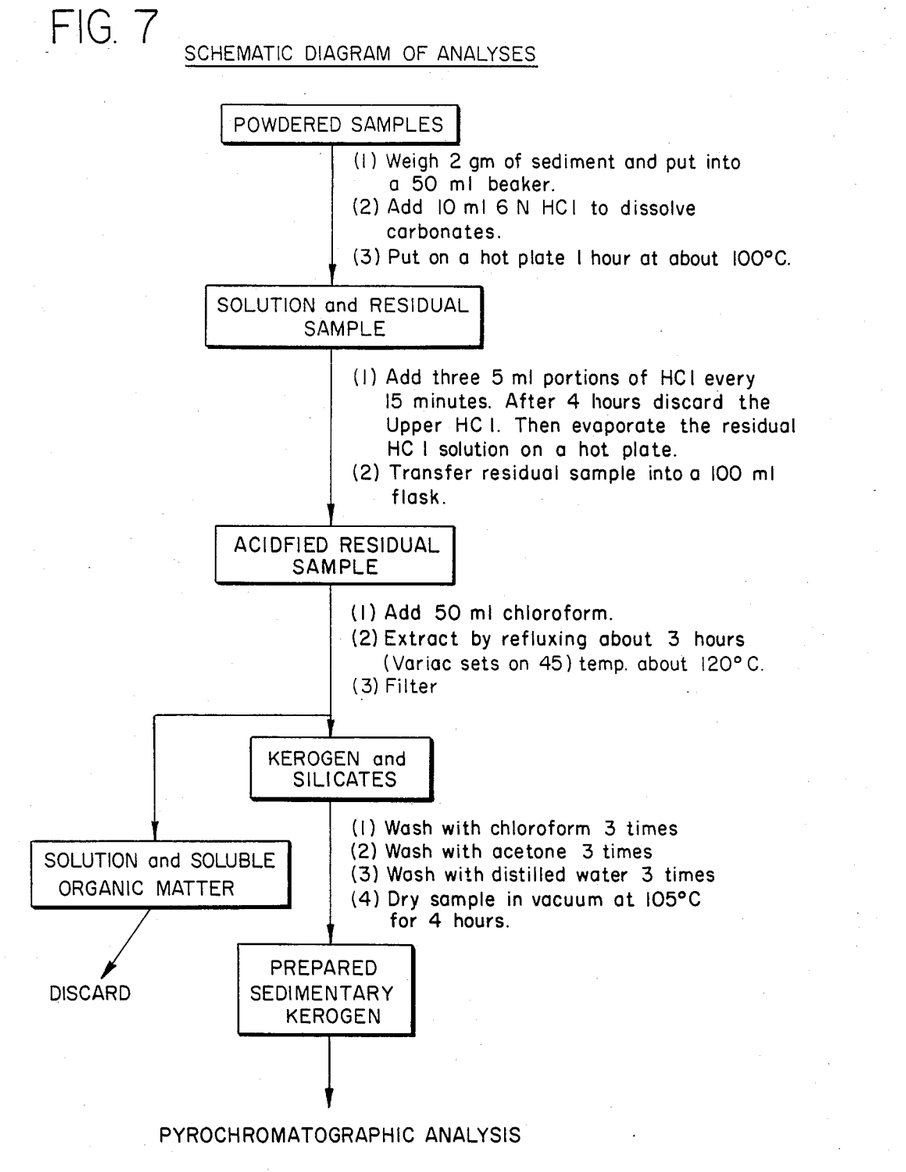
FIG. 7 is a schematic diagram for analysis and sample treatment.

Procedures for sample treatment are illustrated by the schematic diagram of FIG. 7. A general sequence includes: cleaning of the sample; grinding to a powder with a mixer mill; extracting the soluble organic matter with chloroform; pyrolyzing the sample at about 300° C. for about 20 minutes; collecting the evolved hydrocarbons and analyzing said hydrocarbons by a gas chromatograph.

A chromatographic sample injection system for chemical analysis of a kerogenous material is taught in U.S. Pat. No. 4,357,836 issued to F. C. Kokesh on Nov. 9, 1982. This system of sample analysis is hereby incorporated by reference.

To obtain the necessary data, several samples were pyrolyzed at a temperature of from about 250° C. to about 350° C. for about 20 minutes. At this temperature, only small amounts of olefinic hydrocarbons, which are rarely found in crude oils, are generated by thermal cracking. The pyrolytic products resultant therefrom were analyzed by a Gas Chromatograph with a 200-ft. capillary column, coated with Apiezon "L" substrate. Afterwards, weight loss due to pyrolysis and the total organic carbon content of the sediment was measured. Subsequently, the normal hydrocarbons and aromatic hydrocarbons evolved therefrom were collected for each specimen to test for source bed identification.

The components of normal paraffins and aromatic hydrocarbons obtained are listed below into three general categories:

I. Gaseous Hydrocarbons; methane, ethane, propane, and butane.
II. Liquid Hydrocarbons; pentane, hexane, heptane, octane, nonane, decane, and undecane.
III. Aromatic Hydrocarbons; benzene, toluene, meta- and ortho-zylenes.

Figure 1:
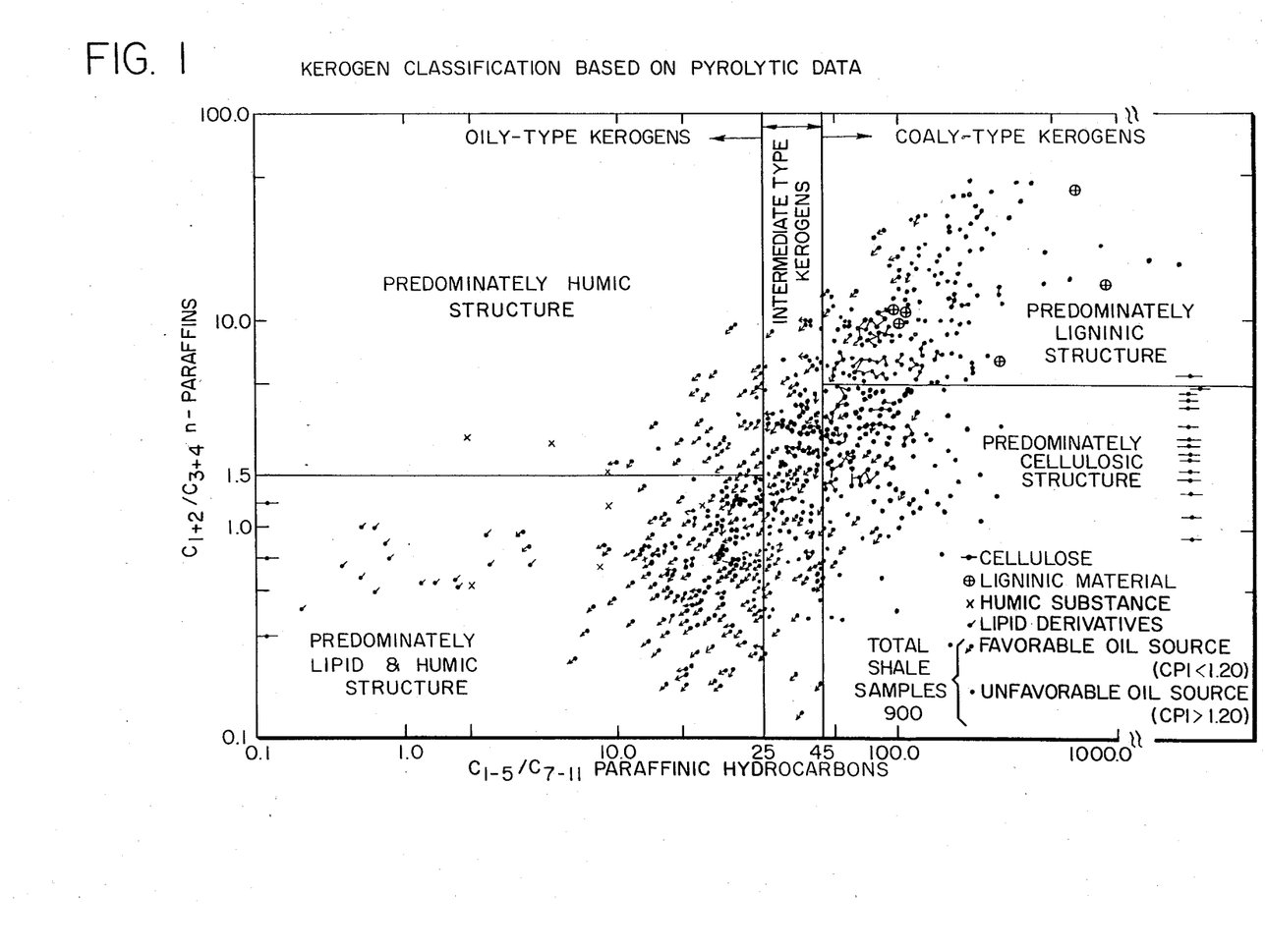
FIG. 1 exhibits a kerogen classification system based on pyrolytic data.

A system for classifying kerogen on the basis of ratios of pyrolytic hydrocarbons is shown in FIG. 1. Separation and classification was based on the ratios of $C_{1-5}/C_{7-11}$ pyrolytic hydrocarbons. By this separation, all kerogens were divided into three groups. Samples with ratios less than 25 have produced pyrolytic hydrocarbons most similar to those yielded by lipid derivatives and humic substances, while a ratio greater than 45 indicates a predominance of pyrolytic hydrocarbons characteristic of cellulosic and ligninic materials. Kerogens of the first group described are termed "oily-type" because of similarities between their organic constituents and rocks that are known to have generated crude oil. The latter group of kerogen is termed "coaly-type" because of compositional similarities with coal. Kerogens with $C_{1-5}/C_{7-11}$ ratios of between about 25 and 45 are considered to be composed of mixtures of oily and coaly kerogen.

Subclassifications within each of the three principal groups are mainly based on ratios of $C_{1+2}/C_{3+4}$ pyrolytic paraffinic hydrocarbons. Kerogens consisting predominantly of molecular skeletons of lipid-derived materials produce gaseous hydrocarbons with $C_{1+2}/C_{3+4}$ ratios less than about 1.50, as do some humic substances. Oily kerogens with $C_{1+2}/C_{3+4}$ ratios greater than about 1.50 are considered to be dominated by humic structures because of the relation of these ratios to those produced by most humic substances. Coaly kerogens with $C_{1+2}/C_{3+4}$ ratios greater than about 5.0 yield abundant methane and ethane and appear to consist predominately of lignin structures because known ligninic substances yield similar pyrolytic hydrocarbons. Kerogens composed predominantly of organic matter with cellulosic structures are within the group of coaly kerogens indicated by $C_{1+2}/C_{3+4}$ ratios less than about 5.0. Within the intermediate group of kerogens, $C_{1+2}/C_{3+4}$ ratios above about 1.5 indicate a predominance of cellulostic substances while ratios below about 1.5 suggest a presence of predominantly humic substances. Three things are to be noted about FIG. 1. First, hydrocarbons are measured by sums of peak heights of each component per mg of sample. Second, pyrolysis of cellulose produces negligible amounts of $C_{5-11}$ n-paraffins. However, any small amounts of $C_{5-11}$ paraffinic hydrocarbons contributed from other parts of kerogen may lead the ratio of $C_{1-5}/C_{7-11}$ n-paraffins into the ranges between 40.0–100.0. Third, humic kerogen can be distinguished from lipid kerogen by the greater quantity of monoaromatics ($C_{5-11}$ n-paraffins/monoaromatics <1.0).

Figure 2:
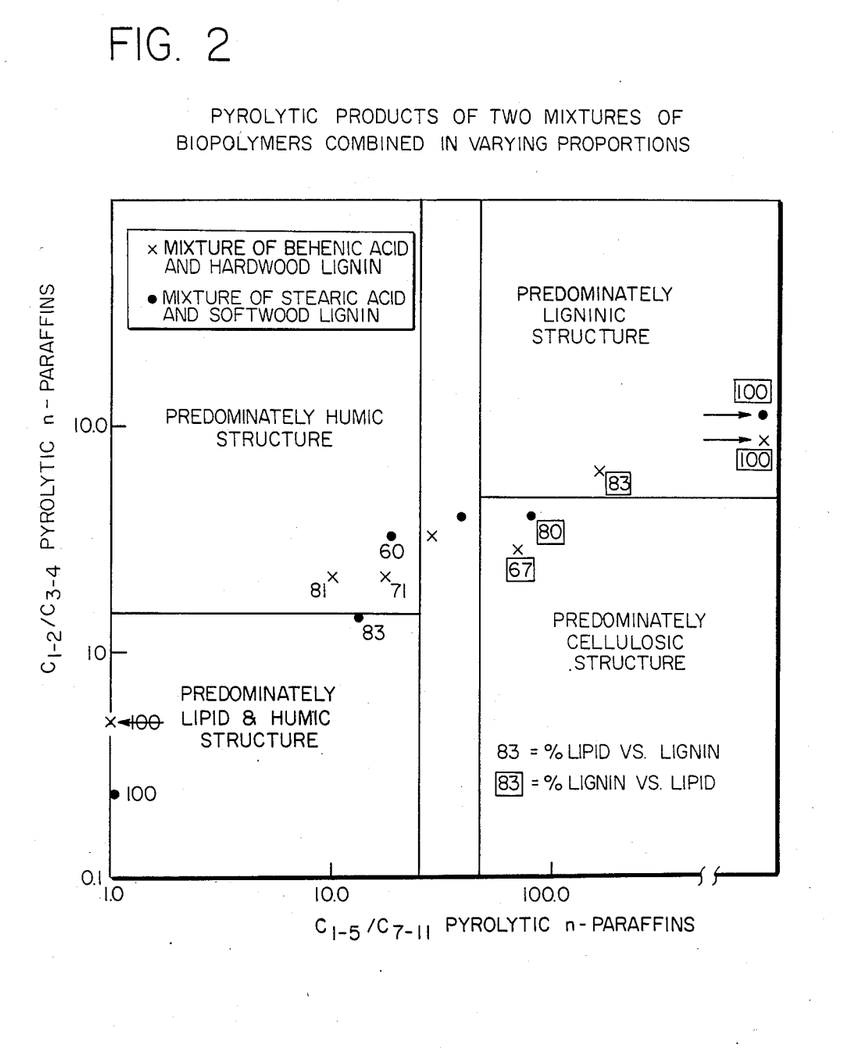
FIG. 2 shows pyrolytic products of two mixtures of biopolymers combined in varying proportions.

Verification in the selection of classification boundaries shown in FIG. 1 is reflected in the results of experiments in which biopolymers were mixed together in known proportions and then pyrolyzed. Simulation of the natural kerogen mixtures (bio-polymers) that are characteristic of shale, the percentage of cellulose in each of the two sets of sample was relatively high (41–49%) and were held constant. These high percentages were obtained because cellulosic structures appeared to be relatively abundant in most shalely kerogens, while the ratios of lipid verus ligninic bio-polymers were caused to range from about 0 to about 100 as indicated in FIG. 2. Cellulosic structures in kerogen generate relatively small amounts of paraffinic hydrocarbons and thus have little influence on kerogen classifications based on pyrolytic normal paraffins. Furthermore, although humic polymers are common in shaly kerogens, the results were not included in FIG. 2 because they are in major part, natural mixtures of unknown proportions of cellulosic, lipid, and ligninic chemical structures. Fundamental polymeric structure (lipids) from which important amounts of liquid paraffinic hydrocarbons are generated and the fundamental structure (lignin) from which important amounts of gaseous paraffinic hydrocarbons are generated were mixed together to see how ratios for the pyrolytic products of the various combinations would be distributed on the classification chart shown in FIG. 2.

The distribution of data points from FIG. 2 conforms very similar to that of natural kerogens as shown in FIG. 1. In FIG. 1, the cloud of data points extends diagonally from the region where lignin pyrolytic products fall into the area where data concerning butumic (lipid) substances are located. This relationship provides evidence that the experimental approach is reasonably valid and that lipid and ligninic polymeric structures are in fact the primary sources of pyrolytic liquid ($C_{7-11}$) or gaseous ($C_{1-5}$) paraffinic hydrocarbons, respectively. Furthermore, ($C_{1-5}/C_{7-11}$) pyrolytic ratios less than about 25 and greater than about 45, correspond to greater than about 60% mixtures of bituminic (lipid) or lignin polymers respectively. This relationship provides reasonable boundary values for defining oil-prone or gas-prone kerogens.

Data have indicated that ratios of pyrolytic hydrocarbons respond with apparent fidelity to compositional changes induced by thermal exposure on a given kerogen. However, a radical alteration of the basic chemical structure of that kerogen is not likely until after an advance stage of thermal maturity, marked by a vitrinite reflectance above about 1.20. The present pyrolytic system therefore provides a basis for not only defining the present basic composition of the kerogen, but also for reconstructing and/or predicting the composition of most kerogens, throughout the immature and mature stages of thermal maturation.

Figure 3:
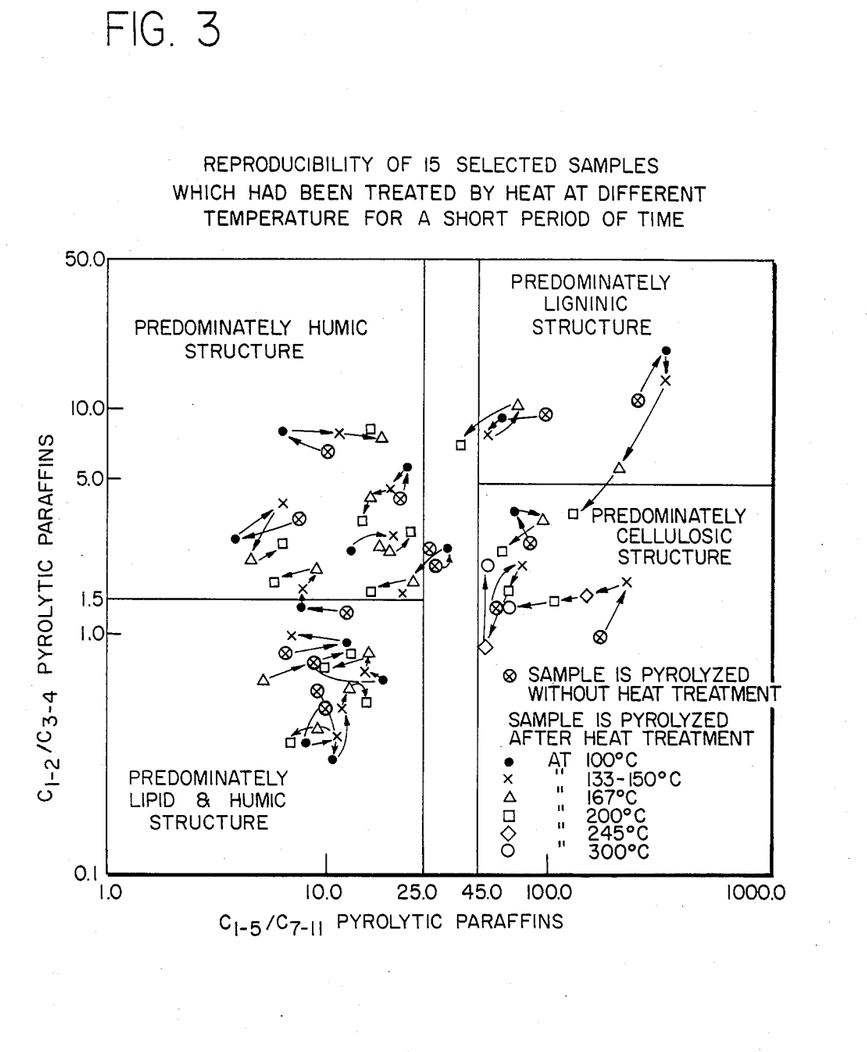
FIG. 3 represents the reproducibility of selected samples which have been treated by heat at different temperatures for short time periods.

This basis has been substantiated, as shown in FIG. 3, from the results obtained by analyzing a group of 15 shales, proportions of which were sealed in individual glass tubes, heated at specific temperatures up to about 300° C. for periods of time ranging from about 48 to about 200 hours, and then pyrolyzed at about 280° C. Pyrochromatographic data for these samples are shown in FIG. 3. Changes in composition of individual kerogens during heating prior to pyrochromatographic evaluation are indicated by displacements of successive data points along the paths shown. Although the actual values of pyrolytic ratios for individual shales change significantly, in most cases the data consistently indicate a single kerogen type according to the proposed classification system.

Figure 4:
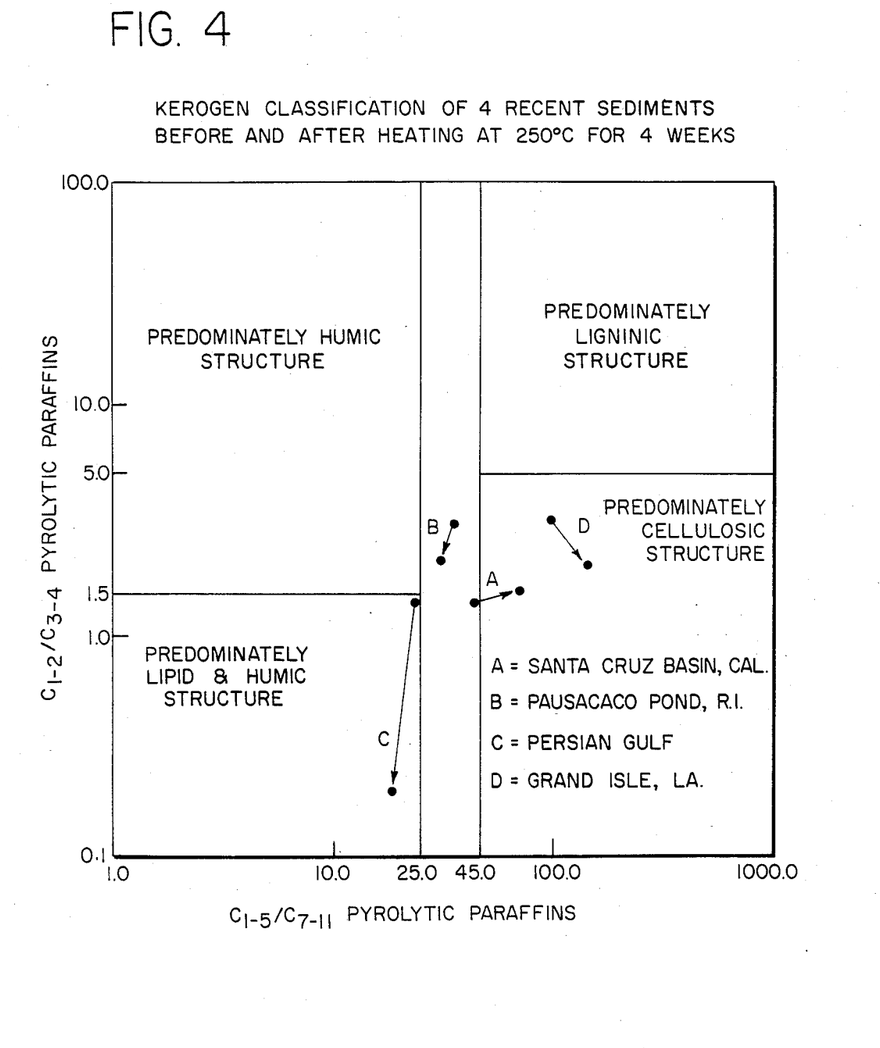
FIG. 4 depicts the kerogen classification of four sediments before and after heating at about 250° C. for four weeks.

Effects of thermal exposure on pyrolytic ratios are shown in FIG. 4. These effects were obtained from test results on four sample sediments. Portions of which were sealed in cylinders and heated to about 250° C. for about 28 days while maintaining a fluid pressure of about 6,000 psi. FIG. 4 illustrates the pyrolytic ratios before and after this episode of artificial diagenesis. As was true in previous experiments where ancient shales were artificially heated, pyrolytic ratios of the modern sediments after heating are sufficiently similar to ratios of the non-heated sediments to indicate that the chemical structure is not drastically changed under these laboratory conditions.

Figure 5:
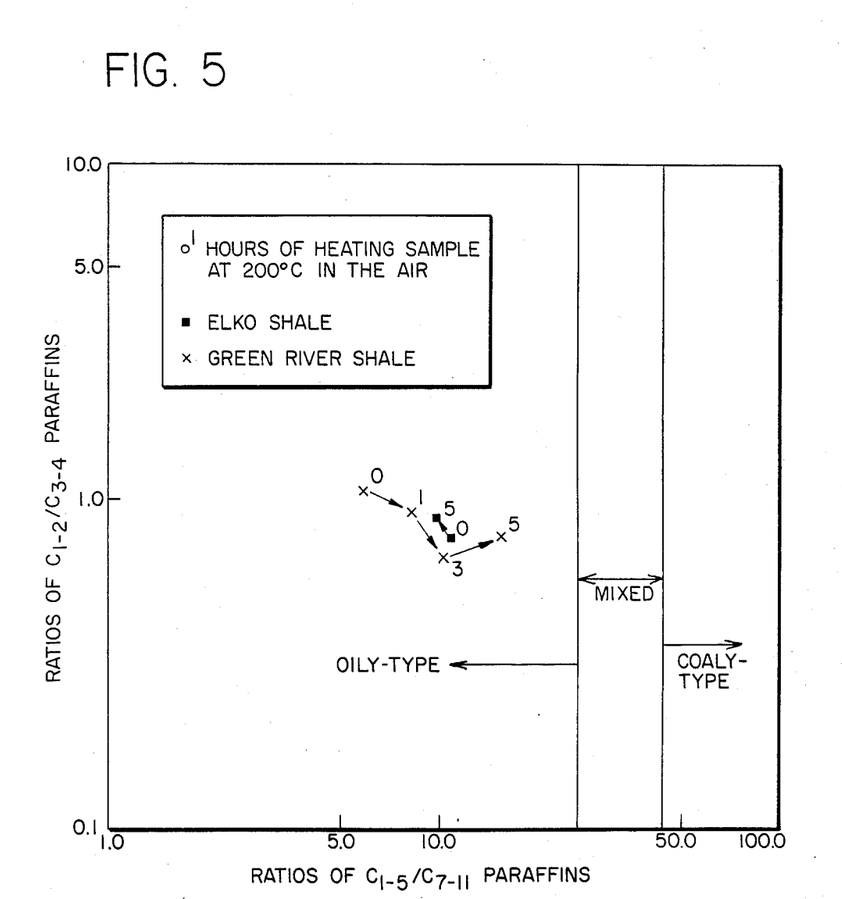
FIG. 5 illustrates the results of heating Elko shale and Green River shale for several hours at a temperature of about 200° C. in air.

Oxidation of organic matter during deposition may alter kerogen constituents and thus vary the primary type of kerogen precursors. To show the effect of oxidation on kerogen constituents, two samples were exposed in the air and heated to about 200° C. up to about 5 hours. The purpose of the elevated temperature was to accelerate the oxidation processes. Pyrolysis of these kerogens indicates that kerogens oxidized at about 200° C. for more than about 3 hours already lost their generation capability. Very small amounts of hydrocarbons, however, can be detected from the pyrograms. Pyrolitic ratios of these kerogens are shown in FIG. 5. A slight change of the ratios can be seen. However, the primary type of kerogen can still be distinctively identified. Based on the relative consistency of pyrolitic ratios representing samples in these three sets of artificially heated samples, it is reasonable to infer that thermal exposure does not drastically alter the fundamental composition of kerogen if the sediment had not been heated at temperatures above 300° C. In order to determine how much additional change in kerogen composition might result from thermal exposure during a longer period of geological time and in a natural environment, another test was run. For this purpose, samples were investigated wherein rocks of uniform lithology have been subjected to a range of natural thermal exposures.

Figure 6:
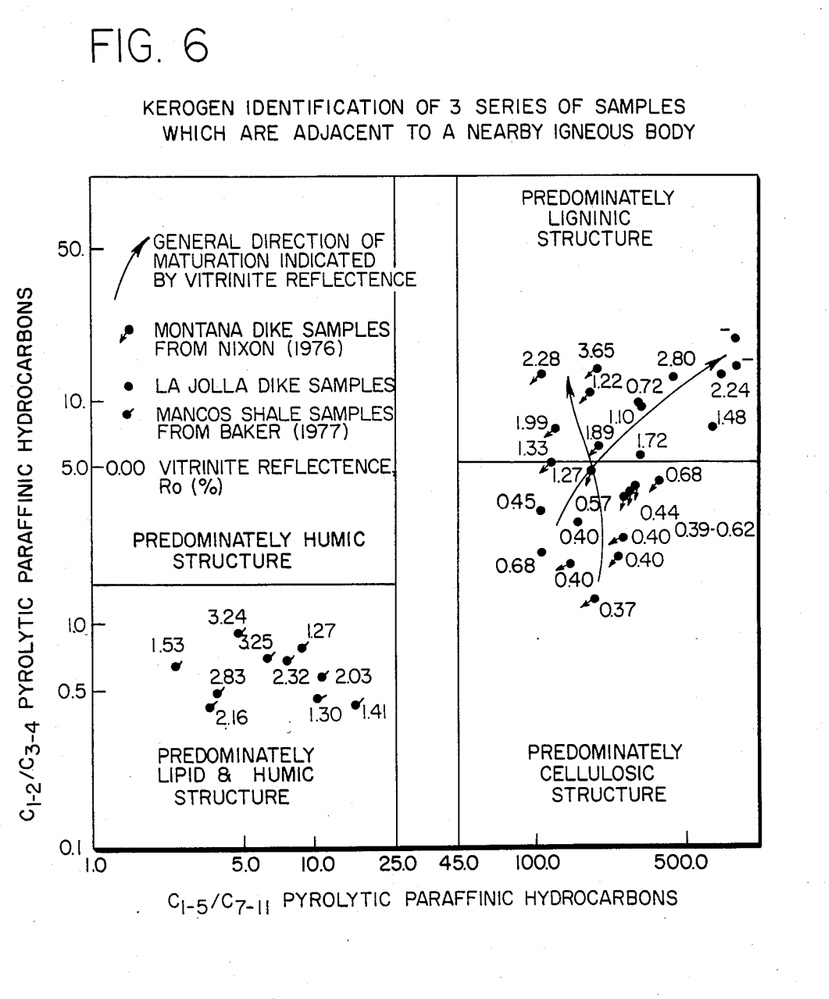
FIG. 6 reflects the kerogen identification of three series of samples which are adjacent to a nearby igneous body.

Three series of samples were collected from sedimentary rock units adjacent to various igneous intrusions. In each case, geological evidence suggested that the samples are from the same or similar stratigraphic units. This indicated that the original composition of organic matter in each individual sample suite was likely to have been uniform. Present differences in kerogen composition between samples in each sample suite are therefore believed to be due to response of the organic matter to thermal exposure. Duration of the heating events connected with the intrusion was not known. However, geochemical and vitrinate reflectance data provided evidence that the organic matter was severely altered in samples collected in rather close proximity with the igneous rocks. As shown in FIG. 6, variations in pyrolitic rituals among samples in each set reveal progressive changes in kerogen composition as maturation progresses. These data suggest that heat-induced changes in kerogen throughout the normal ranges of thermal maturation do not result in a drastic change in chemical structure. Despite extreme differences in thermal maturity, Mancos shale kerogens retain their oil-prone characteristics while kerogens and sediments adjacent to the La Jolla and Montana dikes are consistently classifiable as gas-prone. The stability of pyrolitic ratios enables classification of kerogen and provides a basis for reconstruction and/or projection of their generative characteristics. The stability of ratios of pyrolitic hydrocarbons make them useful in classifying kerogens.

Obviously, many other variations and modifications of this invention, as previously set forth, may be made without departing from the spirit and scope of this invention as those skilled in the art readily understand. Such variations and modifications are considered part of this invention and within the purview and scope of the appended claims.

What is claimed is:

1. A method for classifying kerogenous materials by pyrolyzing a sample containing said material and analyzing the pyrolysis gas by gas chromatography comprising:

(a) pyrolyzing a weighed sample of a crushed raw material of unknown kerogenous content under an inert gas atmosphere at a temperature of from about 250° C. to about 350° C. for about 20 minutes;

(b) determining the ratio of $C_1$–$C_5$ hydrocarbons contained in said pyrolysis gas to $C_7$–$C_{11}$ hydrocarbons;

(c) differentiating said ratios into groups containing a ratio of less than about 25, a ratio of about 25 to about 45, and a ratio of from greater than about 45; and (d) classifying said kerogenous materials according to the three group ratios expressed in step (c) above.

2. The method as recited in claim 1 where in step (c) said ratio of less than about 25 is indicative of pyrolytic hydrocarbons obtained from lipid- and humic-containing kerogenous "oily-type" substances.

3. The method as recited in claim 1 where in step (c) said ratio greater than about 45 is indicative of pyrolytic hydrocarbons obtained from cellulosic and ligninic "coaly-type" kerogenous materials.

4. The method as recited in claim 1 where in step (c) said ratio of from about 25 to about 45 is indicative of a mixture of pyrolytic hydrocarbons obtained from a mixture of "oily-type" and "coaly-type" kerogenous materials.

5. A method for subclassifying lipid, humic, cellulosic and ligninic kerogenous materials by pyrolyzing a sample containing said material and analyzing the pyrolysis gas by gas chromatography comprising:

(a) pyrolyzing a weighed sample of a crushed raw material of unknown kerogenous content under an inert gas atmosphere at a temperature of from about 250° C. to about 350° C. for about 20 minutes;

(b) determining the ratio of $C_1+C_2$ hydrocarbons contained in said pyrolysis gas to $C_3+C_4$ hydrocarbons;

(c) differentiating said ratios into groups containing ratios less than 1.50, and ratios between 1.50 and 5.0, and ratios greater than 5.0; and (d) classifying said kerogenous materials according to the group ratios expressed in step (c) above which provide a basis for reconstruction or projection of the generative characteristics of kerogens.

6. The method as recited in claim 5 where in step (c) the ratio of $C_{1+2}/C_{3+4}$ hydrocarbons is less than about 1.50 and consists predominantly of molecular skeletons of lipid and humic materials.

7. The method as recited in claim 5 where in step (c) the ratio of $C_{1+2}/C_{3+4}$ hydrocarbons is greater than about 1.50 and less than 5.0 and consists predominantly of molecular skeletons of cellulostic derived materials.

8. The method as recited in claim 5 where in step (c) the ratio of $C_{1+2}/C_{3+4}$ hydrocarbons is greater than about 5.0 and consists predominantly of molecular skeletons of lignin.

* * * * *